(12) United States Patent
Coleman

(10) Patent No.: US 7,037,282 B2
(45) Date of Patent: May 2, 2006

(54) FIXED-CIRCUMFERENCE MEDICAL SUPPORT APPLIANCE

(75) Inventor: Richard A. Coleman, Berkeley, CA (US)

(73) Assignee: David G. Coleman, Castro Valley, CA (US)

( * ) Notice: Subject to any disclaimer, the term of this patent is extended or adjusted under 35 U.S.C. 154(b) by 429 days.

(21) Appl. No.: 10/121,970

(22) Filed: Apr. 12, 2002

(65) Prior Publication Data

US 2003/0195449 A1   Oct. 16, 2003

(51) Int. Cl.
*A61F 5/00* (2006.01)

(52) U.S. Cl. .................. 602/5; 602/6; 602/20; 602/23; 128/898; 128/845

(58) Field of Classification Search .............. 602/5–10, 602/4, 20–23, 26; 128/845, 846, 882, 889, 128/878–879, 898

See application file for complete search history.

(56) References Cited

U.S. PATENT DOCUMENTS

| | | | | |
|---|---|---|---|---|
| 3,832,780 A | * | 9/1974 | Lewis | 33/2 R |
| 4,240,414 A | * | 12/1980 | Theisler | 602/26 |
| 4,287,885 A | * | 9/1981 | Applegate | 602/26 |
| 5,036,838 A | * | 8/1991 | Sherman | 602/44 |
| 5,085,210 A | * | 2/1992 | Smith, III | 602/26 |

* cited by examiner

*Primary Examiner*—Michael A. Brown
(74) *Attorney, Agent, or Firm*—Charles L. Thoeming

(57) ABSTRACT

A medical support appliance custom made to fit the patient's limb exactly. Since the appliance fits exactly, it restricts the engorgement of varicose veins and swelling of the limb by retaining its exact shape and dimension, thereby resisting any outward expansion of the limb, and not by pressing in on the limb. The appliance employs an assembly of materials which resists the outward pressure exerted by the veins by retaining its circumference dimensions, and which at the same time stretches longitudinally for comfort and mobility. The assembly is a composite of latex, formed around a replica of the patient's limb, wrapped with non-stretch fiberglass thread, and finished with trim material and a zipper.

4 Claims, 3 Drawing Sheets

FIXED-CIRCUMFERENCE MEDICAL SUPPORT APPLIANCE

BACKGROUND OF THE INVENTION

Varicose veins have vexed humanity throughout recorded history. There are references to varicose veins and the attendant risks of surgery in the Ebers papyrus of 1550 BC. For the working man or woman who must be on their feet much of the day, painful varicose veins can be debilitating. For the athlete, varicose veins can put an early stop to sports activities.

Invasive medical treatments are available and can be effective in some cases. To provide a non-exhaustive summary here, these include stripping (surgical removal of veins), sclerosis (blocking veins via injection of chemical agent or other means), and more recently, venous valve cuffing (implanting devices which reduce circumference of major venous valves). But for the many cases where these treatments are not appropriate or are ineffective, the primary non-invasive medical approach is the application of bandages or elastic hosiery to compress the limb. In the material that follows we will show that this compression approach also has its problems, and that patients who live with this type of treatment will welcome a better solution.

PRIOR ART

Prior art for non-invasive varicose vein relief falls into three major categories: Elastic compression, non-elastic compression, and resistance wrapping.

Elastic-compression

Elastic products include compression hose, compression socks, and graduated compression stockings. The Jobst U.S. Pat. No. 2,574,873 is an early example of compression hosiery. The Swallow U.S. Pat. No. 4,502,301 exemplifies the graduated compression approach, and the Courtney U.S. Pat. No. 5,376,130 uses a slide fastener to close the elastic garment around the limb. The disadvantages of these products are:

Relying on compression or degrees of compression, these products apply constant pressure to the limb whether the patient is sitting or standing.

Although compression force in some of these products may be varied longitudinally, compression is applied uniformly around the circumference of the limb, applying as much pressure to healthy areas as to the problem areas of the limb.

A high degree of compression around the circumference can have the effect of reducing overall circulation in the limb, the tourniquet effect, and when this occurs the garments cannot be worn for extended periods.

They are manufactured to fit a basic range of sizes and often do not fit accurately.

They can be very difficult to apply (put on).

They soon lose their compression qualities and effectiveness through use and washing.

They tend to creep and bunch toward the narrower part of the limb and must be repositioned periodically.

And even the most compressive of these products is not fully effective in preventing venous protrusion for the seriously active person, and most certainly not for the athlete.

Non-elastic Compression

Non-elastic compression products are exemplified by the CircAid-type of legging, reference the Shaw U.S. Pat. No. 5,653,244 and Shaw U.S. Pat. No. 6,109,267. These are leggings of non-elastic cloth construction with Velcro-type (hook and loop) closures. The disadvantages of this type of product are:

Each time it is put on, the patient must determine how hard to pull on the closures and the amount of compression can vary depending on the diligence and motivation of the patient. Although necessary to provide effective compression, the effect of pulling harder on the closures makes the legging stiffer and less comfortable.

Compression force cannot be varied much longitudinally since there are a small number of relatively large closures.

Compression is applied uniformly around the circumference of the limb, applying as much pressure to healthy areas as to the problem areas of the limb.

Although more durable than elastic compression hosiery and also more costly, effective life of these products also is limited due to use and washing.

Resistance Wrapping

Resistance wrapping is exemplified by the traditional Unna boot, first described in 1854 and named for its inventor. With this technique, the patient's limb is wrapped in plaster tape and the hardened cast is allowed to remain for no more than a week or until a symptom such as a venous ulcer is mitigated. Although useful for healing of venous ulcers, the Unna boot approach is not appropriate for providing ongoing support for an ambulatory patient since the patient is partially immobilized by the plaster cast, the cast is vulnerable to water, and the useful life of the cast is very short.

Another example of a medical wrapping that does not in itself use compression is the Latenser U.S. Pat. No. 4,494,536 Foam Boot. Said Foam Boot provides a protective cushion, but does not independently provide support to the limb nor prevent swelling or venous protrusion.

BRIEF SUMMARY OF THE INVENTION

Advantages over prior art are as follows:

The support appliance described here does not apply constant pressure to the limb. Constant pressure is avoided because the appliance is the exact size of the person's limb before the limb has become enlarged or engorged from the effects of gravity.

The support appliance acts to hold the limb in its pre-engorged state acting against the effects of gravity through restriction rather than compression. The surface veins themselves are not compressed, merely held to their pre-engorged shape and size. The patient does not experience any of the discomfort associated with elastic compression systems.

The support appliance wraps around the limb and is quickly zipped into position with no difficult rolling and fighting against elastic tension.

The support appliance will not slip down or out of position even under the most rigorous of athletic activities. It is the perfect appliance for athletes or anyone who spends a good deal of time on their feet.

The support appliance will not degrade structurally by washing. Effectiveness of the appliance is retained even after constant use and repeated washings, and it can last several years.

The above advantages are realized due to a unique application of standard materials, which provides the fixed circumference needed to support the veins while allowing vertical flexibility.

LIST OF REFERENCE NUMERALS

Figure 1:
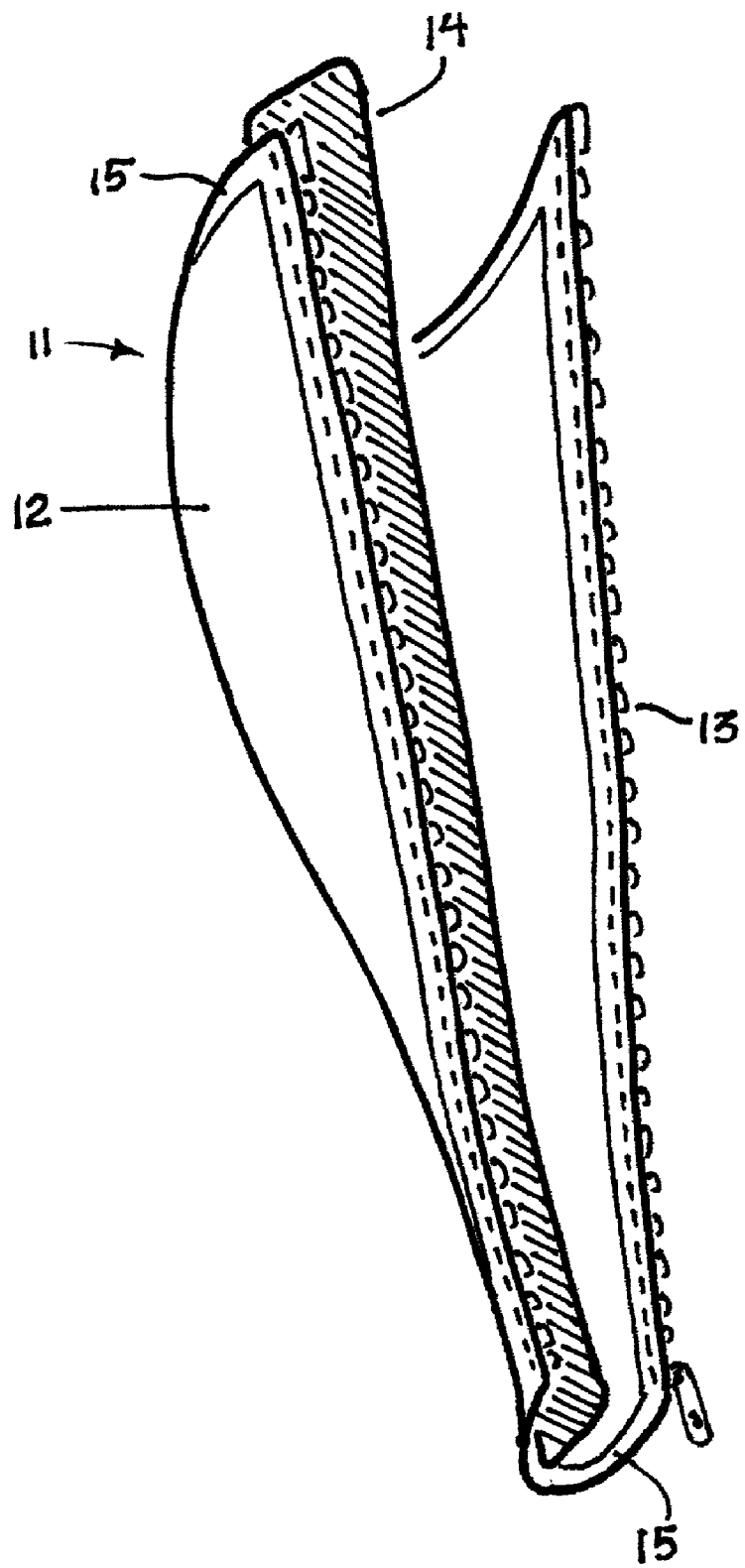
FIG. 1 shows the support appliance unzipped and ready for use by the patient.
Figure 2:
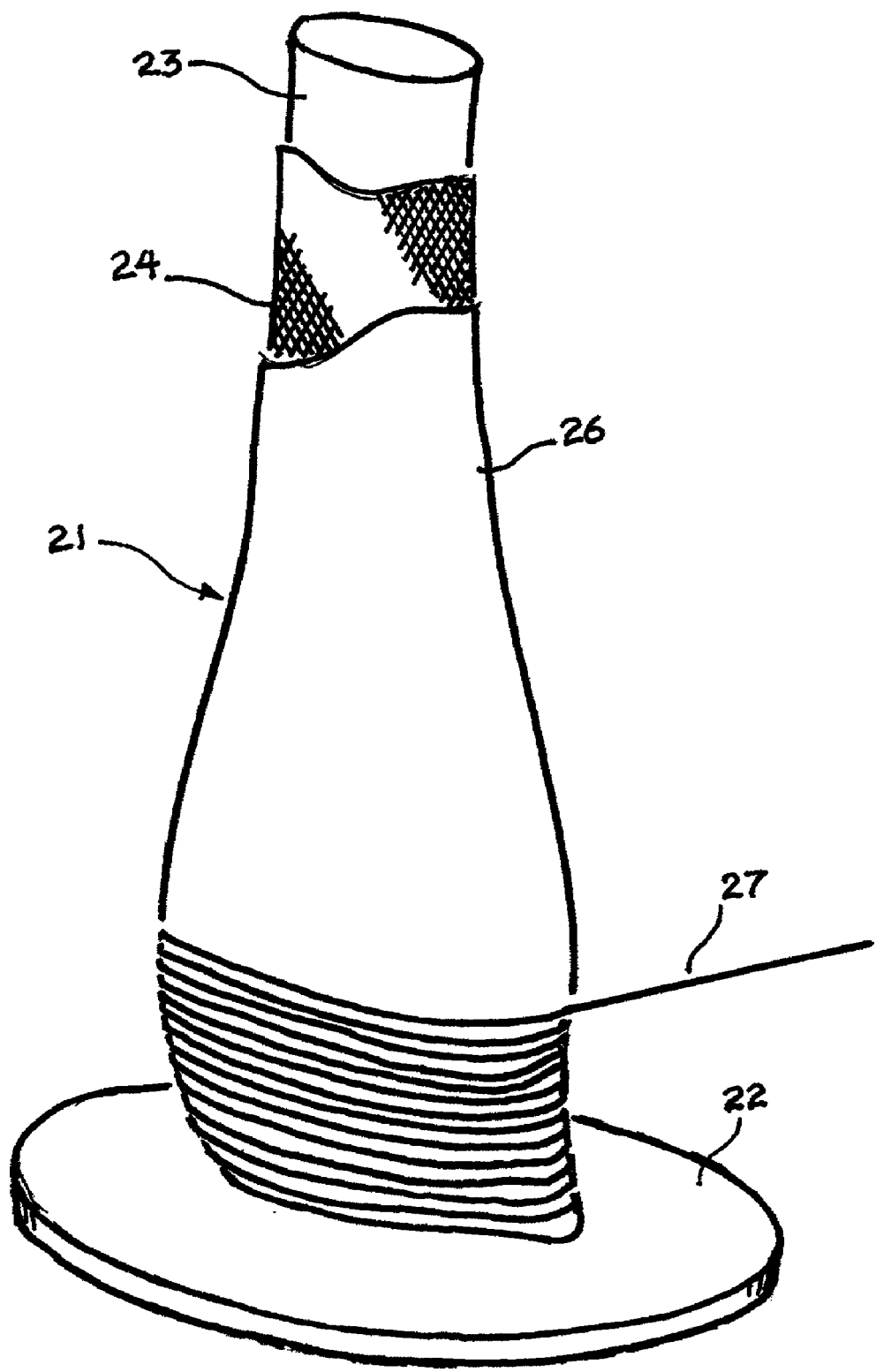
FIG. 2 is a view of the appliance during assembly showing non-stretchable thread being wound around the assembly. The view is partially cut-away to show underlying components.
Figure 3A:
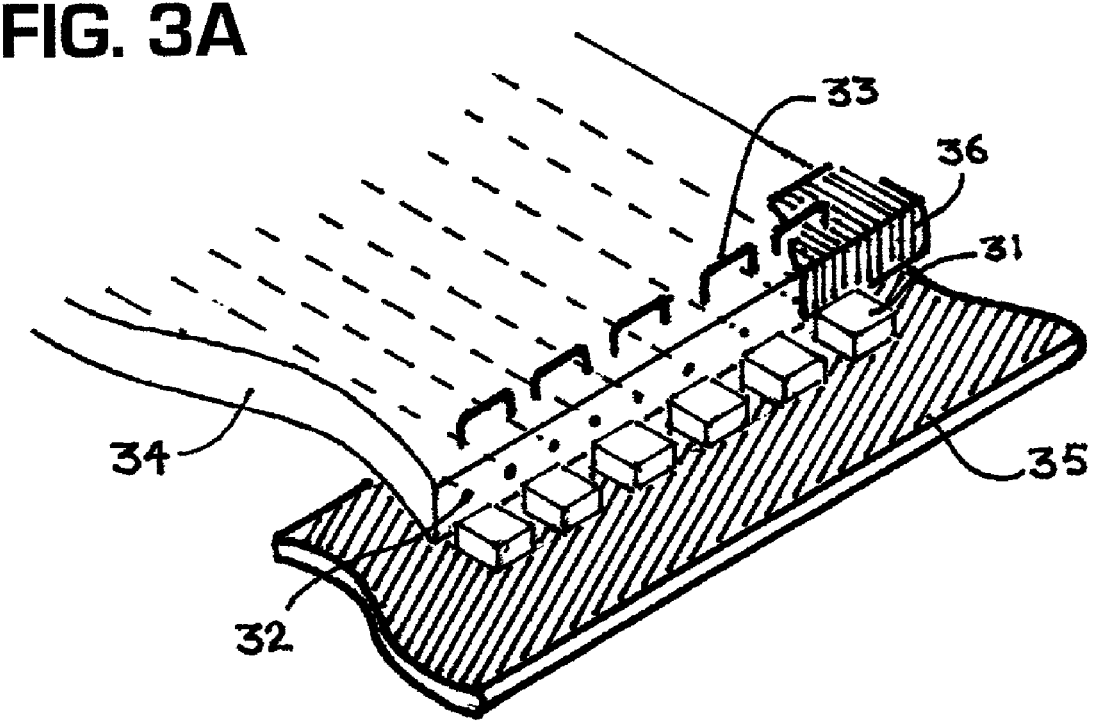
FIG. 3A is a perspective cross-section view showing installation of the zipper closure and additional capture of the non-elastic threads.
Figure 3B:
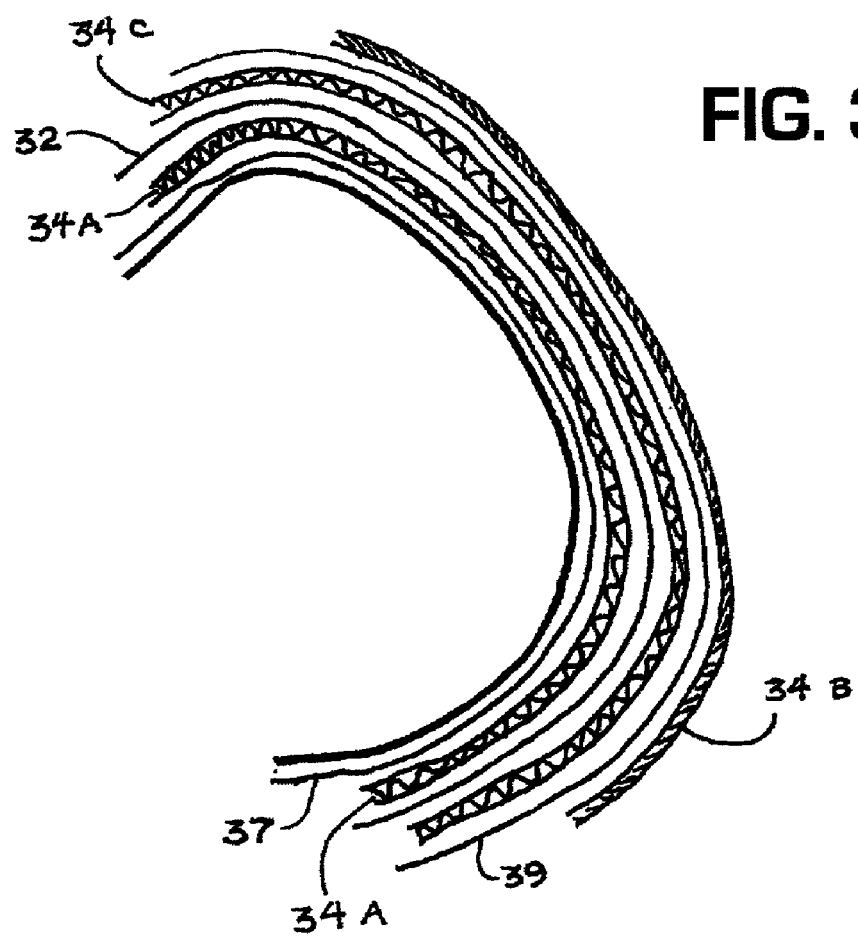
FIG. 3B is an exploded cross section view of the support appliance showing components and their relative locations.

FIG. 1
11 Support Appliance Overall
12 Latex Layers
13 Zipper Closure
14 Protective Flap
15 Trim Pieces
FIG. 2
21 Support Appliance Overall
22 Turntable
23 Replica of Limb
24 Inner Nylon Stocking
26 Latex Layers
27 Non-stretch Fiberglass Thread
FIGS. 3A and 3B
31 Zipper
32 Non-stretch Threads
33 Longitudinal Stitching
34 Latex Layers
34A Latex Layers (Base)
34B Latex Layers (Outermost—colored)
34C Latex Layers (Additional over non-stretch threads)
35 Protective Flap
36 Edging
37 Inner Nylon Stocking
39 Outer Nylon Stocking

DETAILED DESCRIPTION OF THE INVENTION

The support appliance 11 shown in FIG. 1 is made of layers of latex 12, formed to match the dimensions and shape of the patient's lower leg. The appliance is shown with zipper closure 13 unzipped and ready for use. To use the appliance, the patient wraps it around their lower leg with the opening in front, then engages and closes the zipper. The protective flap 14 protects the patient's skin from any abrasion by the zipper. The trim pieces 15 surround the edges of the assembly. When closed, non-stretch threads FIG. 2 27 locked within the latex cause it to maintain its circumferential dimensions, supporting the limb, expansion, and preventing protrusion of varicose veins. Firmness of the assembly and accurate fit to the limb prevent it from shifting downward or bunching at narrower parts of the limb. Flexibility of the latex longitudinally provides a level of comfort and mobility that allow it to be worn all day, every day, by even the most active patient.

A crucial art of the assembly process is depicted in FIG. 2, which shows the support appliance 21 mounted on a turntable 22. The cut-away portion shows the replica of the limb 23 and the inner nylon stocking 24. At this stage of assembly, a plurality of latex layers 26 has been built-up and the outermost layer is not fully cured and therefore still in a semi-adhesive state. Non-stretch fiberglass thread 27 is shown being wrapped around the assembly and embedded within the outermost layer of latex. Distance between strands of thread is approximately from ⅛ to ¼ inch.

FIG. 3A is a cross-section in perspective intended to show in detail how sewing-in of the zipper 31 acts to further capture the cut ends of the non-stretch threads 32. The longitudinal stitching 33 used to install the zipper is shown intersecting the non-stretch threads. This capture of the non-stretch threads, in addition to their capture by the semi-adhesive latex, prevents the threads from pulling loose within the latex 34 thereby ensuring that they continue to preserve the fixed circumference of the appliance. The zipper 31, protective flap 35, and edging 36 are placed together and sewn to the cut edge of the assembly with longitudinal stitching which intersects the non-stretch threads.

The relative locations of the composite layers of the completed appliance are shown via the cross-section view in FIG. 3B. The innermost layer is the inner nylon stocking 37, which provides a smooth and comfortable surface for the appliance. Next is a base of latex 34A, which provides shape and structure for the appliance while allowing flexibility. Around the base of latex are wound non-stretch fiberglass threads 32, which prevent the circumference of the appliance from increasing while it is worn by the patient. An additional latex layer 34C is applied over the non-stretch threads. The outer nylon stocking 39 covers the non-stretch threads, smoothing the surface of the assembly. The outermost latex layer 34B is of the desired color and provides a durable and washable exterior surface for the appliance.

Preferred Method for Construction

The support appliance is constructed via the following steps:

1. A plaster cast is made of the subject limb or portion of limb.

Where the foot or lower leg is involved, the cast must be made when the patient has had their feet elevated for about an hour, or other time when the subject veins are not yet engorged. The limb is either shaved or coated with a thin layer of petroleum jelly to facilitate removal of the cast. The limb is wrapped with wet plaster casting tape and then allowed to dry. When dry, the cast is cut in two pieces longitudinally using a cast removal saw. At this point the patient's involvement is completed until the support appliance is delivered.

2. A positive replica is made of the limb or portion of limb.

Each half of the negative (concave) cast taken from the patient is coated with a release agent. Liquid plaster is then poured into the cast and allowed to dry. When dry, the positive replica is coated with shellac to seal the plaster.

3. A composite layer is built-up around the positive replica.

The positive replica is mounted on a turntable (lazy-Susan or potter's wheel-type device) to facilitate working with all surfaces. A nylon stocking is pulled over the positive replica to provide a smooth interior surface for the appliance and to provide a base for the assembly. Liquid latex is brushed onto the assembly rotating the turntable as needed to provide access to all surfaces. Several coats of latex (3 or 4) are applied, each coat being allowed to dry before applying the next. Based on the appearance of the positive and noting where venous protrusion occurs, additional liquid latex is applied in these places where additional strength may be required. After 3 or 4 coats of latex have been applied and the last coat is still not fully cured and is still slightly adhesive, the entire length of the appliance is wrapped around the circumference with a thread of fiberglass or other non-stretching material. While the turntable is rotated, the thread is wrapped with a gap of ⅛ to ¼ inch between successive strands. To provide additional strength in locations where venous protrusion occurs, the gap is gradually reduced to 1/16 of an inch. A nylon stocking of color as close as possible to the desired color is selected, and the nylon stocking is pulled over the assembly to cover the wrapped threads and to provide a smooth surface. Two coats of very thin liquid latex of the desired color are then brushed onto the assembly and allowed to dry.

4. The appliance is trimmed and fitted with a zipper.

The assembly of composite layers is cut away from the positive replica using a single cut. For leg appliances, the cut is along the shin. Excess latex is trimmed from the ends and edging is sewn on. A fixed amount of material is trimmed from the longitudinal cut to allow for material introduced by the zipper. The zipper is then sewn in with a neoprene flap underneath, the longitudinal seam intersecting the cut ends of the non-stretch threads. Sewing of edging and zipper is done with a walking-foot sewing machine since a substantial thickness of material must be penetrated.

Use

The support appliance is used as follows:

The appliance is worn directly on the skin. It can be worn under socks, pants or other clothing. It is difficult to put on after the limb has become swollen or the veins engorged, so it should be put on early in the day or other time before swelling is likely to occur. It can be worn all day.

The appliance should be hand washed periodically in warm water with a mild detergent and allowed to air dry. It should not be immersed in very hot water (too hot to touch), machine washed, nor placed in a clothes dryer.

RAMIFICATIONS AND SCOPE

The most obvious ramification is the improved quality of life for patients with varicose veins. The inventor of the appliance described here has used prototypes of the appliance personally for over four years and is very pleased with the results.

It is anticipated that due to the need to make a plaster cast of the patient's limb, obtaining a support appliance will of necessity involve a clinician in a clinical setting. The implication is that the appliance will become an additional option available to the clinician, and it is they who will prescribe or recommend the appliance to the patient.

Regarding scope, the appliance can be applied also to lymphedema patients to prevent swelling, and to amputees to prevent swelling of residual limb or stump.

What is claimed is:

1. A method for construction of a medical support appliance, the method comprising the steps of:

making a positive replica of a patient's limb;

applying a plurality of layers of flexible material over said positive replica;

wrapping non-stretchable thread or other non-stretch stranded material around the circumference of said flexible layers, building up an assembly of materials;

cutting said assembly longitudinally and installing a zipper or other closure;

whereby the resultant assembly becomes an effective medical support appliance capable of supporting said patient's limb preventing venous protrusion, allowing easy use and removal of said appliance, and providing comfort and flexibility of movement for said patient.

2. A method for construction of a medical support appliance as in claim 1 wherein said layers of flexible material are formed using liquid latex.

3. A method for construction of a medical support appliance, the method comprising the steps of:

making a positive replica of a patient's limb;

applying a plurality of layers of flexible material over said positive replica;

wrapping non-stretchable thread or other non-stretch stranded material around the circumference of said flexible layers while the outermost layer is still in a semi-adhesive state, thus building up an assembly of materials with non-stretchable threads captured within the flexible material;

cutting said assembly longitudinally and installing a zipper or other closure by sewing a longitudinal seam which in addition to affixing said closure also intersects said non-stretchable threads additionally capturing them within said assembly, thus preventing later displacement of said non-stretchable threads within said assembly;

whereby the resultant assembly becomes an effective medical support appliance capable of supporting said patient's limb preventing venous protrusion, allowing easy use and removal of said appliance, and providing comfort and flexibility of movement for said patient, and ensuring durability of said appliance.

4. A method for construction of a medical support appliance as in claim 3 wherein said layers of flexible material are formed using liquid latex.

* * * * *